United States Patent [19]
Andersen et al.

[11] Patent Number: 5,674,276
[45] Date of Patent: Oct. 7, 1997

[54] TUBULAR MEDICAL PROSTHESIS

[75] Inventors: Erik Andersen, Roskilde, Denmark; Ernst Peter Strecker, Karlsruhe, Germany

[73] Assignee: Boston Scientific Corporation, Natick, Mass.

[21] Appl. No.: 283,985

[22] Filed: Aug. 1, 1994

Related U.S. Application Data

[60] Division of Ser. No. 912,902, Jul. 13, 1992, Pat. No. 5,366,504, which is a continuation-in-part of Ser. No. 886,518, May 20, 1992, Pat. No. 5,405,378.

[51] Int. Cl.$^6$ .................................. A61F 2/06; A61F 2/04
[52] U.S. Cl. .................................. 623/1; 623/11; 623/12
[58] Field of Search .................................. 623/1, 11, 12; 600/36; 606/194, 195, 198, 151–158

[56] References Cited

U.S. PATENT DOCUMENTS

| | | |
|---|---|---|
| 3,657,744 | 4/1972 | Ersek . |
| 4,130,904 | 12/1978 | Whalen . |
| 4,140,126 | 2/1979 | Choudhury .................................. 623/1 |
| 4,164,045 | 8/1979 | Bokros et al. . |
| 4,300,244 | 11/1981 | Bokros . |
| 4,327,736 | 5/1982 | Inoue . |
| 4,626,255 | 12/1986 | Reichart et al. . |
| 4,708,141 | 11/1987 | Inoue et al. . |
| 4,717,387 | 1/1988 | Inoue et al. . |
| 4,733,665 | 3/1988 | Palmaz . |
| 4,739,762 | 4/1988 | Palmaz . |
| 4,776,337 | 10/1988 | Palmaz . |
| 4,798,585 | 1/1989 | Inoue et al. . |
| 4,816,029 | 3/1989 | Penny, III et al. . |
| 4,820,298 | 4/1989 | Leveen et al. .................................. 623/1 |
| 4,840,635 | 6/1989 | Smith et al. . |
| 4,892,539 | 1/1990 | Koch .................................. 623/1 |
| 4,922,905 | 5/1990 | Strecker . |
| 4,990,158 | 2/1991 | Kaplan et al. . |
| 4,994,071 | 2/1991 | MacGregor . |
| 5,015,253 | 5/1991 | MacGregor .................................. 623/1 |
| 5,147,400 | 9/1992 | Kaplan et al. . |

FOREIGN PATENT DOCUMENTS

| | | |
|---|---|---|
| 0 335 341 | 10/1989 | European Pat. Off. . |
| 0 364 787 | 4/1990 | European Pat. Off. . |
| 0 441 516 | 5/1991 | European Pat. Off. . |
| 0 461 791 A1 | 12/1991 | European Pat. Off. . |
| 1 173 811 | 12/1969 | United Kingdom . |
| 2 225 034 | 5/1990 | United Kingdom . |
| WO 92/06734 | 4/1992 | WIPO . |
| 9206734 | 4/1992 | WIPO .................................. 623/1 |
| WO 92/09245 | 6/1992 | WIPO . |

OTHER PUBLICATIONS

Guidoin et al., "Albumin Coating of a Knitted Polyester Arterial Prosthesis: An Alternative to Preclotting" *The Annals of Thoracic Surgery*, vol. 37, No. 6, Jun. 1984, pp. 457–465.

Mitchell et al., "Comprehensive Assessment of the Safety, Durability, Clinical Performance, and Healing Characteristics of a Double Velour Knitted Dacron Arterial Prosthesis", *Vascular Surgery*, vol. 14, No. 3 May/Jun. 1980, pp. 197–212.

Koopmann et al., "Degenerative Changes in Dacron External Velour Vascular Prostheses", *J. Cardiovas. Surg.*, vol. 21, No. 2, Mar.–Apr. 1980, pp. 159–162.

Kim et al., "Dilation of Synthetic Grafts and Junctional Aneurysms", *Arch. Surg.*, vol. 114, No. 11, Nov. 1979, pp. 1296–1303.

(List continued on next page.)

*Primary Examiner*—Debra S. Brittingham
*Attorney, Agent, or Firm*—Fish & Richardson, P.C.

[57] ABSTRACT

A tubular prosthesis including a tubular wall portion of loosely interlocked pattern, e.g. of knitted loops, constructed to function within a body lumen. The loops are preferably formed of co-knitted strand materials. A first strand material is a metal strand that structurally defines the tubular shape of the prosthesis and maintains the shape when positioned in the lumen. A second strand material is a predetermined substance selected to provide desired characteristics to the wall of the prosthesis.

12 Claims, 11 Drawing Sheets

OTHER PUBLICATIONS

May et al., "Multiple Aneurysms in Dacron Velour Graft", *Arch. Surg.*, vol. 113, No. 3, Mar. 1978, pp. 320–321.

Robicsek et al., "Indium 111–Labeled platelet deposition in woven and knitted Dacron bifurcated aortic grafts with the same patient as a clinical model", *Journal of Vascular Surgery*, vol. 5, No. 6, Jun. 1987, pp. 883–837.

Rousseau et al., "Self–expanding Endovascular Prosthesis: An Experimental Study", *Radiology*, vol. 164, No. 3, Sep. 1987, pp. 709–714.

Carson et al., "Recurrence of Femoral Anastomotic Aneurysms", *The American Journal of Surgery*, vol. 146, (1983), pp. 774–778.

Harris et al., "A Comparative Study of Selected Physical Properties of Aortic Homografts and Heterografts", *Journal of Thoracic and Cardiovascular Surgery*, vol. 57, No. 6, Jun. 1969, pp. 830–833.

Schatz et al., "Report of a New Articulated Balloon Expandable Intravascular Stent (ABEIS)", *Circulation Supplement*, vol. 78, No. 4, Oct. 1988, p. II–449.

Schatz et al., "Report of a New Radiopaque Balloon Expandable Intravascular Stent (RBEIS) in Canine Coronary Arteries", *Circulation Supplement*, vol. 78, No. 4, Oct. 1988, p. II–448.

Alvarado et al., "Evaluation of Polymer–Coated Balloon–Expandable Stents in Bile Ducts", *Radiology*, vol. 170, No. 3, Mar. 1989, pp. 975–978.

Bailey et al., "Polymer Coating of Palmaz–Schatz Stent Attenuates Vascular Spasm After Stent Placement", *Circulation Supplement*, vol. 82, No. 4, Oct. 1990, p. III–541.

Kram et al., "Optical Synthetic Grafts for Aortic Replacement", W.B. Saunders Company, pp. 339–350.

Wesolowski et al., "The Compound Prosthetic Vascular Graft: A Pathologic Survey", *Surgery*, vol. 53, Jan.–Jun., 1963, pp. 19–44.

Chapman et al., "A Bioabsorbable Stent: Initial Experimental Results", *Supplement III Circulation*, vol. 82, No. 4, Oct. 1990, p. 0283.

Waller et al., "Vessel Wall Pathology After Angioplasty", *Cardio*, Aug. 1990, pp. 57–72.

Kinley et al., "Compliance: A Continuing Problem with Vascular Grafts", *J. Cardiovas. Surg.*, vol. 21, No. 2, Mar.–Apr. 1980, pp. 163–170.

Clark et al., "Mismatch of Mechanical Properties as a Cause of Arterial Prostheses Thrombosis", *Surgical Forum*, pp. 208–210.

Nöldge et al., "Modelling of Transjugular Intrahepatic Portosystemic Shunts (TIPSS) With Stents", *Radiology* vol. 31, No. 3, Mar. 1991, pp. 102–107.

Sauvage et al., "Future Directions in the Development of Arterial Prostheses for Small and Medium Caliber Arteries", *Surgical Clinics of North America*, vol. 54, No. 1, Feb. 1974, pp. 213–228.

Hall et al., "Velour Fabrics Applied to Medicine", *J. Biomed. Mater. Res.*, vol. 1, No. 2, Jun. 1967, pp. 179–196.

Lindenauer, "The Fabric Vascular Prosthesis", *V/Vascular Grafts*, pp. 450–460.

Medi–tech, Boston Scientific Corporation, Strecker Stent product literature.

Applicant's knowledge of knit fishing lures.

Lawrence, David D. Jr., "Percutaneous Endovascular Graft: Experimental Evaluation", RADIOLOGY, vol. 163, No. 2, May 1987, pp. 357–360.

International Search Report for PCT Application No. PCT/US93/06529 (mailed Oct. 20, 1993).

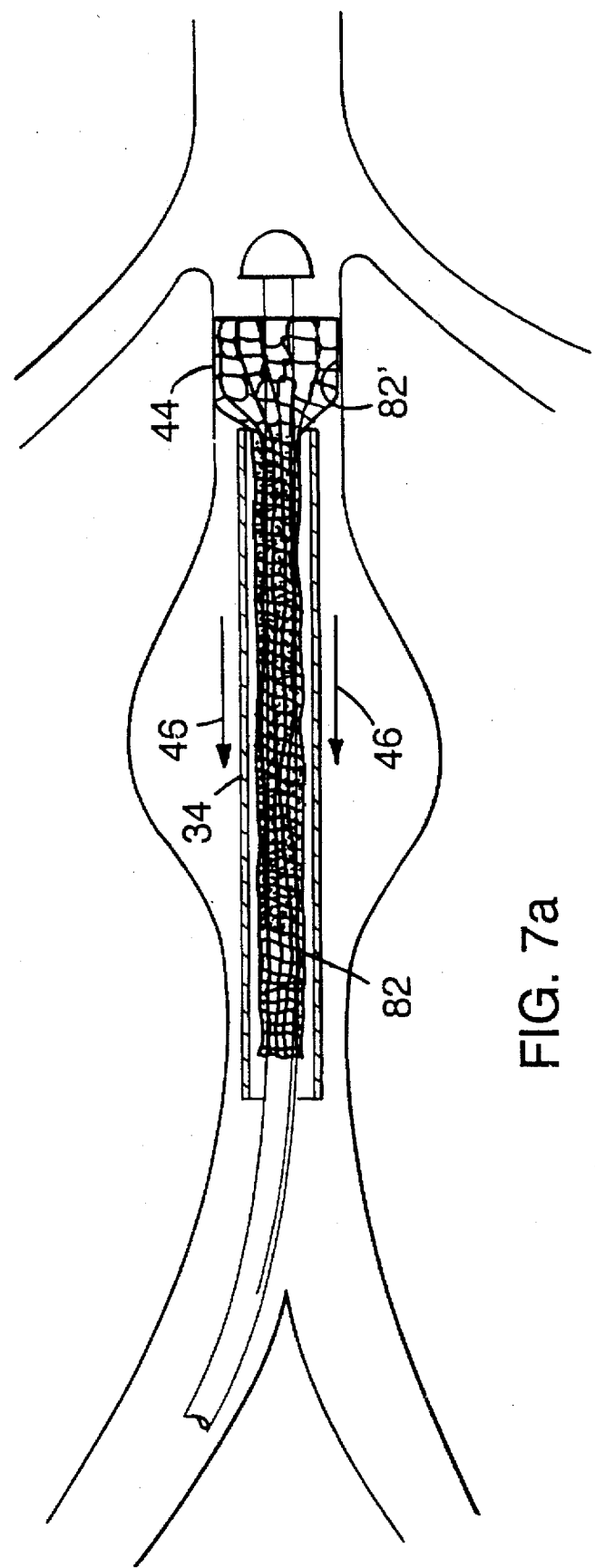

TUBULAR MEDICAL PROSTHESIS

CROSS-REFERENCE TO RELATED APPLICATIONS

This is a divisional of copending application Ser. No. 07/912,902, filed Jul. 13, 1992, now U.S. Pat. No. 5,366,504 which is a CIP of Ser. No. 07/886,518, filed May 20, 1992, now U.S. Pat. No. 5,405,378.

FIELD OF THE INVENTION

This invention relates to tubular prostheses which are placed within the body.

BACKGROUND OF THE INVENTION

Tubular prostheses are used in body lumens to perform various functions. For example, a tubular stent may be used to maintain the opening of an esophagus that has been restricted by a tumor or a blood vessel restricted by plaque. Tubular grafts are used to substitute for or reinforce a weakened lumen, such as the aorta or other blood vessel that has been weakened by an aneurysm. In this latter technique, a graft of a knitted dacron may be used to advantage since the textured nature of the textile can induce blood clotting along the graft to contribute to the patency of the lumen formed by the graft.

Tubular prostheses for purposes such as the above may be positioned in the body lumen during a surgical procedure or may be delivered into the body by a catheter that supports the prosthesis in a compact form during percutaneous insertion and transport through body passageways to a desired site. Upon reaching the site, the prosthesis is expanded so that it engages the walls of the lumen. After this operation, the catheter is removed, leaving the device in the body.

The expansion technique may involve forcing the prosthesis to expand radially outwardly, for example, by inflation of a balloon carried by the catheter. Knitted, balloon expandable stents are discussed for example in Strecker U.S. Pat. No. 4,922,905, the entire content of which we hereby incorporate by reference. In another technique, the prosthesis is formed of an elastic material that can be arranged and held in a compact form for insertion and allowed to expand when in position by its own internal elastic restoring force. Knitted self-expanding stents are described in Strecker PCT EP 91/02194 and in Anderson U.S. Ser. No. 07/773,847, filed Oct. 9, 1991, the entire contents of both applications being incorporated herein by reference.

SUMMARY OF THE INVENTION

The invention provides prostheses with improved properties by forming the prostheses of multiple filaments or strands of different materials, one of which is a structural filament, preferably metal. In preferred embodiments, the strands are knit into a tubular form. In some embodiments, multiple strands of different materials are co-knit into a stent. The term "co-knit" as used herein refers to the knitting of multiple discrete strands in the knit pattern. In certain preferred embodiments, the strands are in a parallel co-knit form, by which is meant the strands of the various substances lie in parallel in all contiguous loops of the co-knit portion of the knit pattern. In other embodiments, the multiple strands of different materials are alternately knit such that adjacent rows of knit loops are of the different materials. In some embodiments, different regions of the prosthesis are formed of different sets of materials. In still further embodiments, a tubular structure of a first knit material is provided as a sheath over a second tubular structure of another knit material.

In one particular aspect, the invention features a tubular prosthesis having a tubular wall portion of loosely interlocked knitted loops constructed to function within a body lumen. The loops are formed of co-knitted strand materials where a first strand material of the loops is a metal wire that structurally defines the tubular shape of the prosthesis and maintains the shape when positioned in the lumen and a second strand material of the loops is co-knitted with the metallic strand and is formed of a predetermined substance selected to provide desired characteristics to the wall of the prosthesis.

In another particular aspect, the invention features a vascular graft prosthesis for bridging an aneurysm in an arterial lumen of the body. The graft has a tubular wall portion of loosely interlocked knitted loops constructed to function within the arterial lumen. The loops are formed of co-knitted strand materials where a first strand material of the loops is a metal wire that structurally defines the tubular shape of the prosthesis and maintains the shape when positioned in the lumen and a second strand material of the loops, co-knitted with the metallic strand, is formed of a predetermined non-metallic substance selected to provide desired characteristics to the wall of the prosthesis to enable it to perform its the function to effectively provide a patent covering over the structure of the graft.

In another particular aspect, the invention features a vascular prosthesis for use in an arterial lumen of the body. The prosthesis has a tubular wall portion of loosely interlocked knitted loops constructed to function within the arterial lumen. The loops are formed of parallel co-knitted strand materials where a first strand material of the loops is a metal wire that structurally defines the tubular shape of the prosthesis and maintains the shape when positioned in the lumen and a second strand material of the loops, co-knitted with the metallic strand, is a textured textile strand substance selected to enhance patency characteristics of the wall of the prosthesis.

In another particular aspect, the invention features a tubular prosthesis. The prosthesis has a tubular wall portion of loosely interlocked knitted loops constructed to function within a body lumen. The loops are formed of multiple strand materials where a first strand material of the loops is a metal wire that structurally defines the tubular shape of the prosthesis and maintains the shape when positioned in the lumen and a second strand material of knitted loops is formed of a predetermined substance selected to provide desired characteristics to the wall of the prosthesis.

In yet another particular aspect, the invention features a tubular prosthesis. The prosthesis has a tubular wall portion of a loosely interlocked regular pattern of strands constructed to function within a body lumen. The pattern is formed of multiple strand materials where a first strand material of the pattern is a metal wire that structurally defines the tubular shade of the prosthesis and maintains the shape when positioned in the lumen and a second strand material of the pattern, integrated with the metallic strand as part of the pattern, is formed of a predetermined substance selected to provide desired characteristics to the wall of the prosthesis.

The features of the above aspects can be combined. In addition, various embodiments may include one or more of the following features. The prosthesis has an anchoring end portion of knitted loops which are knitted integrally with at least a portion of the co-knitted wall portion and formed of a strand material adapted to make contact with the wall of the body lumen to maintain the axial position of the prosthesis in the body lumen. The anchoring end portion is formed of contiguous loops of the first, metal strand material joined integrally with the the wall portion that includes the co-knit second strand. The anchoring end portion of the prosthesis is self-expanding and is formed of elastic metal strand capable of being reduced in radial size without plastic deformation and retaining self-restoring capability such that the end portion can be reduced to a relatively small size for introduction lengthwise into the lumen, and when freed can radially self-expand to tubular form to engage the wall of the lumen. The anchoring end portion is formed of the plastically deformable metal and is knit integrally with the wall portion. The anchoring end portion is formed of metal strand flared to a diameter greater than the wall portion. The prosthesis has an anchoring portion at each of its axial ends. The wall portion is expandable to desired size by means of an internal expanding force or is self-expanding. The first strand material of the wall portion is a plastically deformable metal and the wall portion is expandable to a desired size by application of an internal expanding force. The first strand is selected from tantalum and nitinol. The second strand is selected from dacron, wool, nylon, polyethylene and teflon. The material of the second strand is textured to induce blood clotting. The prosthesis is sized for use as an aortic graft having, for example a porosity of about 4000 ml/min or more at implantation. The second strand is formed of a body fluid-dissolvable suture material. The second strand is an absorbing member that includes a drug. The second strand material is a metal, such as a dense metal that enhances the radiopacity of the prosthesis. The co-knit strands are in a parallel co-knit pattern. The first strand material and second strand material are continuously, single knitted to form regions of the tubular knit structure formed of the first material and regions of the knit structure formed of the second material. The first and second strand materials are alternately knitted to form successive alternating loop rows of the first and second material. The first and second strand materials are formed as separate knitted loop tubular structures and the second strand knitted loop structure extends coaxially with the first strand knitted loop structure and extends over an end of the first strand knitted loop structure to form a cuff to secure the first knitted structure to the second knitted structure. Rather than knitting, the tubular prosthesis pattern is formed by co-weaving or co-crocheting the strands, such as into a pattern formed of multiple parallel strands.

The invention also includes methods for manufacture and use of the prostheses described. Still other aspects of the invention will be understood from the following description and from the claims.

DESCRIPTION OF THE PREFERRED EMBODIMENT

We first briefly describe the drawings.

Drawings FIG. 1 is a side view, in magnified scale, of an aortic graft prosthesis according to the invention using two different strand materials co-knit into a tubular structure in parallel co-knit fashion, while FIG. 1a is a greatly expanded view of adjacent loops in the wall portion of the graft of FIG. 1

FIG. 3 is a side view of another prosthesis according to the invention, while

FIGS. 5 and 5c is a side view of another prosthesis according to the invention, while

FIG. 6 is a diagrammatic view of a circular knitting machine configured for alternate knitting while

DESCRIPTION

Figure 1:
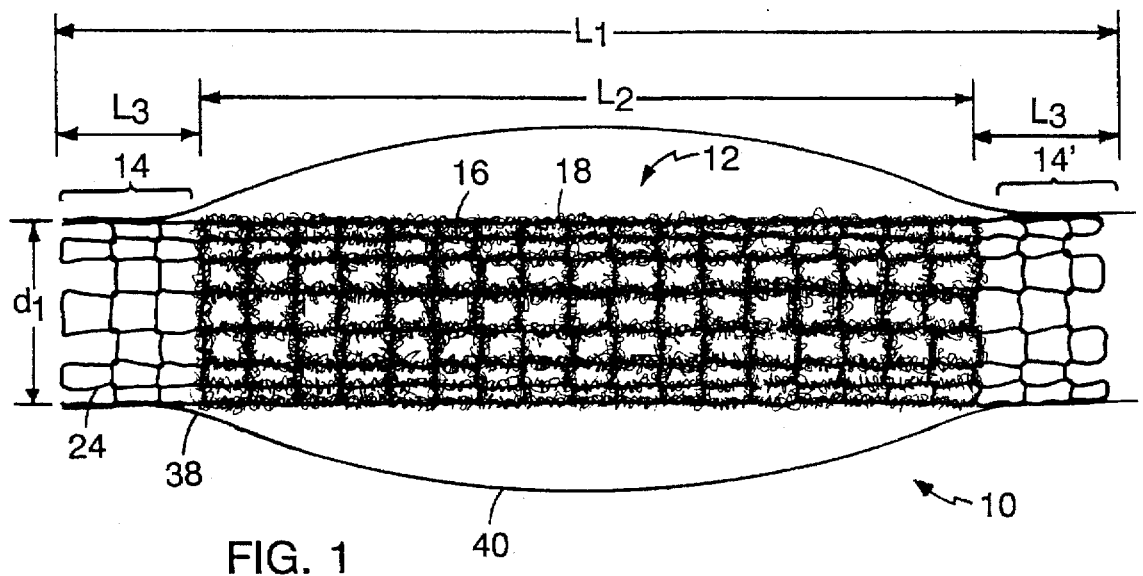
Figure 1A:
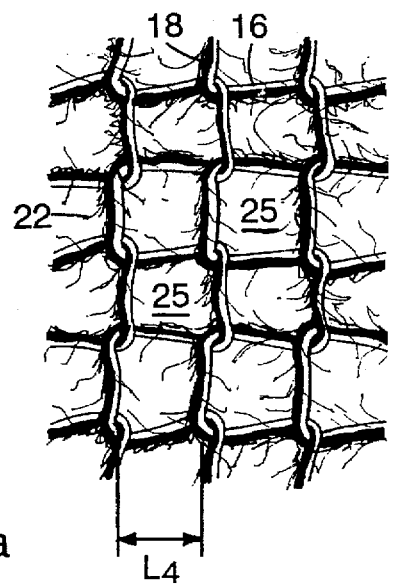

Referring to FIGS. 1 and 1a, an embodiment of a prosthesis according to the invention is a graft 10 which may be positioned in the abdominal aorta 38 within an aneurysm 40. The graft 10, of overall length $L_1$, e.g., about 8 cm, includes a wall portion 12, of length $L_2$, e.g., about 5 cm, that spans the aneurysm 40 and anchoring end portions 14, 14', each of length $L_3$, e.g., about 1.5 cm, that engage healthy portions of the aorta to anchor the prosthesis in the lumen. As illustrated, the graft 10 is formed of loosely interlocked knitted loops of material. The diameter $d_1$ of the graft 10 and the respective lengths are variable, as discussed below, to accommodate various aorta diameters and aneursym conditions. For example, the diameters may be in the range of 10–20 mm and prosthesis lengths $L_1$ in the range of about 4–8 cm.

Referring particularly to FIG. 1a, in the wall portion 12, the loops are formed by parallel co-knitting of a first strand material 16, a metal, and a second strand material 18, preferably of texturized filament or fiber. The first strand material substantially defines the tubular structure of the graft and is a selected metal strand of wire such as tantalum. The second strand material 18 is preferably non-metallic, e.g. a polymer or natural textile fiber or the like, such as a textile yarn, selected to provide a desired characteristic of the prosthesis to enable it to perform a desired function. In the case of an aortic graft, the second material is selected for its capability of inducing the clotting of blood. In these embodiments, the second strand material 18 is preferably a texturized material such as dacron yarn formed of crimped or texturized multiple monofilaments, typically in excess of about 20, with multiple, randomly extending segments 22 that extend into the open area 25 between adjacent knitted loops.

The anchoring portions 14, 14' are formed of wire knitted strand 24, that does not include a co-knit strand. Strand 24 is integral with the wall portion 12 and may be a knitted extension of the metal strand material 16. (Alternately, the anchoring end portions may be a co-knit structure which may De the same or different from the co-knit structure of the central wall portion.)

A particular aspect of this embodiment is parallel co-knitting to form rather loosely interlocked loops with selected, loop length, $L_4$, e.g. about 1.8 mm that provides substantial open area 25. This design facilitates wrapping the prosthesis into small size for delivery intralumenally. Wrapping produces a sliding action of adjacent loops within the open area that avoids stress concentrations in the wires, yet the size of the open area and texturized nature and number of strands formed of the second material provides strand components that extend within the open areas of the loops. By suitable selection, these components can be sufficient to produce clotting in a sufficiently short time that excessive bleeding through the graft will not occur when the graft is placed inside the lumen. A particular benefit of this design is that, generally, the graft need not be pre-clotted before placement. Over time in the body, the graft accepts cells, endothelializes and becomes a patent portion of the artery. The porosity of the graft may be, e.g., about 4000 ml/min or more at implantation. This degree of porosity facilitates migration of cells (e.g. fibroblasts and endothelial cells) into and through the knit structure such that cellular structure can be formed. (Graft porosity as measured by water filtration testing is discussed, for example, in Wesolowski, S.A. Dennis, C., *Fundamentals of Vascular Grafting*, New York, McGraw-Hill, 1963.)

Further, the loosely interlocked loops formed by the co-knitting process of metal wire and the other selected substance are free to slide with respect to each other while in use in the body. This ability for the loops to slide enhances the ability of the device to maintain its axial working length and resist migration when the prosthesis is locally radially compressed. Under such compression the loop structure may locally lengthen or shorten to accommodate similar changes in the vessel in which it is installed, as may occur for instance if the aorta is stretched. The loosely co-knitted structure also allows the graft to negotiate tortuous vasculature during delivery on a catheter because of its flexibility longitudinally.

The co-knitting has other advantages as well. For instance, it provides a mechanism for attachment of multiple strand materials without need for additional means such as tie strands and the like, although these optionally may be employed.

One embodiment of a graft as in FIG. 1 and 1a employs, in parallel with the metal strand, four parallel strands of dacron (44DTEX), each strand consisting of 27 filaments, full drawn R02 medical grade (available from E.I. DuPont de Nemours and Co., Wilmington, Del.). Before co-knitting, the strands are texturized by false twisting and set by radiation heating. Parallel co-knitting with a tantalum wire strand (0.10 mm) is carried out to produce a 10 mm diameter ($d_1$) graft with a circumferential loop count of 12 loops and a wall portion of 4 cm length ($L_2$) consisting of 29 co-knit rows and anchoring end portions, of 10 single knit rows of tantalum. The loop length of the knitted loops in the axial direction is about 1.8 mm.

Other Embodiments

Generally, the principle of combining different strands to form a prosthesis provides a ready ability to adapt the properties of the stent to suit various applications, the respective strands being selected to provide properties which enhance performance. In general, at least one of the strands will be selected for its structural properties to enable the stent to maintain an open passage. In many preferred embodiments such strands are of selected metal. The metal strand material may be of a metal selected to enhance radiographic visualization of the prosthesis during the delivery through a body lumen, the positioning at a desired site and the assessing of the efficacy of treatment. Particular advantages are achieved when the metal strand is formed of a highly radiopaque metal such as tantalum. The metal strand material also may be selected for features relating to its expandability, to enable a single size-prosthesis to be manufactured for use in lumens of somewhat varying size as may be encountered from patient to patient. The metal strand material may be a metal capable of yielding when the stent is expanded in the lumen by an internal radial force, such as by balloon expansion. Such a prosthesis is therefore size-selectable for the desired application. In other cases, the metal strand material is selected to form an elastically self-expanding prosthesis which may be reduced to a small diameter for introduction into the body and allowed to expand at a desired site by release of a restraint. Embodiments in this case would use an elastic metal strand such as nitinol wire, which also can enhance maintenance of the elasticity of the vessel in which it is placed and can be used to widen an occluded vessel. For example, the prosthesis may be used as a stent in the biliary duct or the esophagus to widen these ducts in the cases where they have been occluded by tumors. In the case of stents formed by co-knitting another strand with a self-expanding elastic metal, the co-knit portions may still require balloon expansion because of the restraining effect of the second strand, or to ensure good seating. The metal strand may also comprise a two component cored material as discussed in U.S. Ser. No. 07/861,253, filed Mar. 31, 1992, the entire contents of which are hereby incorporated by reference.

The second strand material may be a wool, nylon, polyester, polyethylene or teflon, selected e.g. for the degree of texture desired. Various embodiments may also include a strand adapted for drug delivery. The second strand material may also be a dissolvable suture material or an absorbent such as hollow absorbent material carrying drug that inhibits body rejection of the prosthesis or inhibits hyperplasia. The drug may be slowly releasable as the strand dissolves, finally leaving only the thin metal first strand to provide desired reinforcing structure through the loops of which healthy endothelial tissue can gradually grow without the chaffing or grinding effects that might occur at points of intersection of the strands that have dissolved. In other embodiments, both the first and second strands are metals that provide different desirable properties. For example, one strand may be an elastic material such as nitinol and the second strand a dense radiopaque strand such as tantalum that enhances the fluoroscopic visibility of the device. Preferably, in these latter embodiments, one or both of the metal strands include a polymer coating to avoid electrolytic corrosion induced by contact of dissimilar metals in an aqueous body fluid environment. The coating may be selected to be dissolvable. A drug may be incorporated in the coating so that, by the dissolving action, the drug is released over time. The rate of dissolution of a coating may be selected so that removal of the coating occurs at a desired time, to enable electrolytic corrosion to dissolve one of the strands, thereby to reduce the amount of metal remaining in the body. The coating may also be seeded with fibrin on the surface to control a fibrin layer with the aim of forming neuro intima. A strand material employing a semipermeable membrane for drug delivery can also be used. One such material is described in EP 0441516, published Aug. 8, 1991, the entire contents of which is hereby incorporated by reference.

Different portions of a prosthesis can be tailored with specific, different properties, to achieve different functions, by using various strands of different materials at different locations, which are easily implemented during the knitting process. As illustrated above in FIGS. 1 and 1a, the anchoring portions 14, 14' can be, for example, axial knitted extensions of the metal strand material 16 which may be produced by ceasing co-knitting of the second strand material at a desired point in production. In some cases a second metal strand which can be of the same or different properties from the first metal can be added in this region to strengthen the anchoring portions or for other purposes.

In certain cases of an aortic graft, as discussed above with respect to FIGS. 1 and 1a, it is particularly advantageous not to have clot-producing strands in the anchoring region so that substantial clotting will not be induced at the end portions where it is not necessary and the mechanical properties of the metal strand can perform their function unimpeded to provide secure anchorage. The strands at the end portions may be selected to be elastic, self-expanding, or plastically deformable.

Alternatively, the metal strand at the anchoring ends may be a different strand material than either the first strand material or second strand material in the main body or wall portion of the stent, to produce a desired effect, such as self-expandability in the anchoring ends and balloon expandability in the wall portion. The anchoring end material can be co-knit to overlap with a portion of the wall portion.

Figure 2:
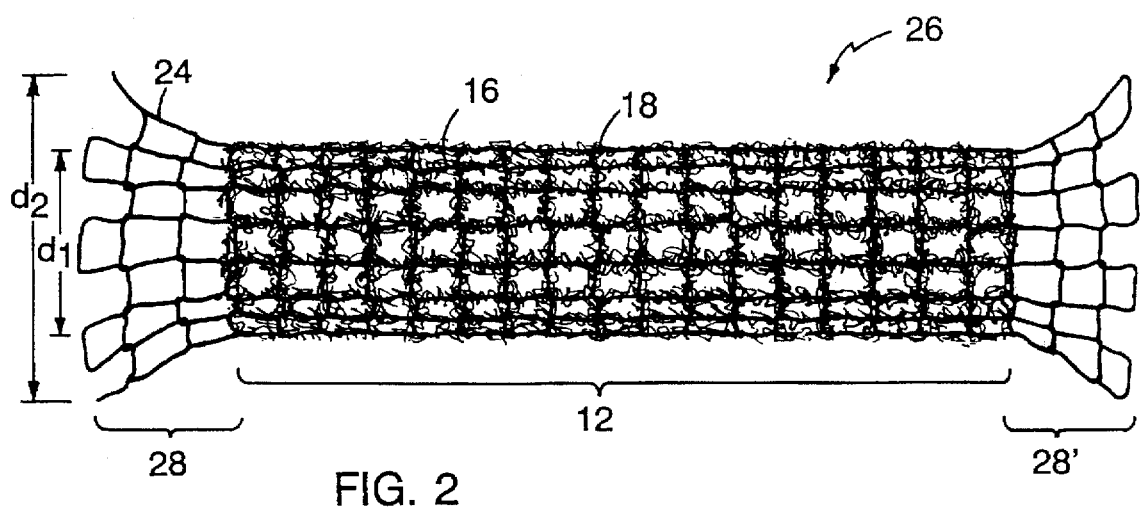
FIG. 2 is a side view of another prosthesis according to the invention.

Referring to FIG. 2, a prosthesis 26 is illustrated having a wall portion 12 and anchoring ends 28, 28'. In this embodiment ends 28, 28' are flared outwardly to a diameter, $d_2$, such that they impress upon the inner wall of a body lumen 2 for anchoring the prosthesis 26 in place. As with the embodiments above, the strands 25 at the anchoring ends may be selected to make the ends self-expanding or expanded by plastic deformation by an internal expansion device.

Figure 3:
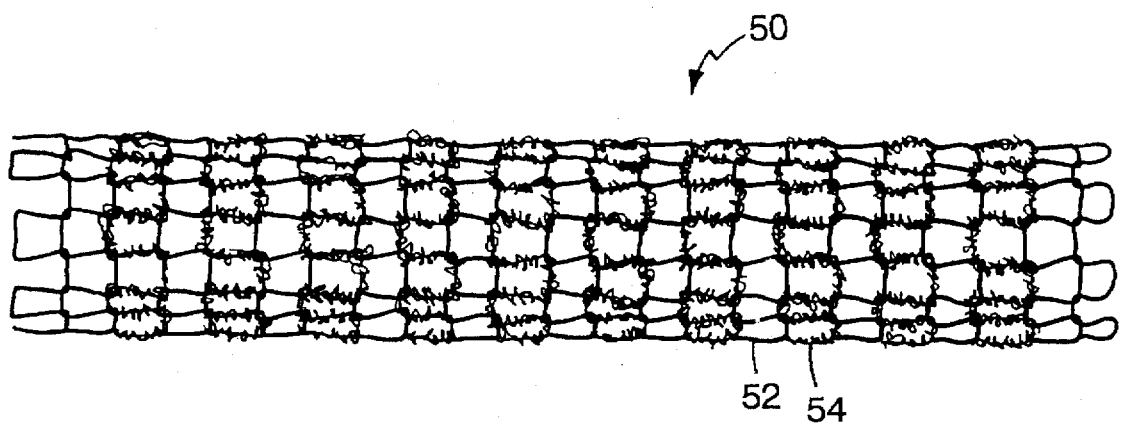
Figure 3A:
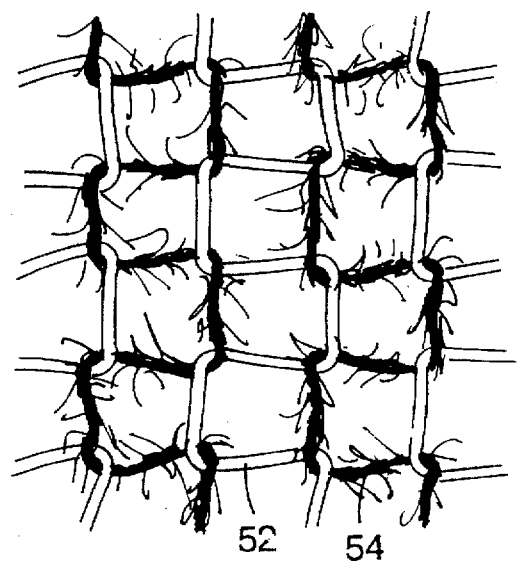
FIG. 3a is an enlarged view of a portion of the prosthesis of FIG. 3.

Referring to FIGS. 3 and 3a, in another embodiment, rather than parallel co-knitting, a stent 50 may be formed by continuous knitting a first strand material 52 and a second strand material 54 in an alternating, sequential co-knit fashion to form adjacent spiral patterns of loops along the length of the stent, resulting in successive alternating rows of different material in a single knit structure. In preferred embodiments, strand 52 is a metal strand, most preferably tantalum, and second strand 54 is a dissolvable, resorbable thread of material such as is used in dissolvable sutures. In a predetermined time, in the body, the thread strand 54 is dissolved leaving only circumferential rings of successive loops of metal which avoids strand intersections that could exert shearing forces or other damaging effects on surrounding and growing tissue. In preferred embodiments, drugs e.g., an antiproliferative, can be embedded in the dissolvable strand to gradually deliver the drug to surrounding tissue as the strand dissolves. In an alternative preferred embodiment, the first strand is a metal selected for its elastic properties and the second strand is a radiopaque metal, with one or both of the metals including a coating to inhibit, at least temporarily, the electrolytic degradation of the strands, as mentioned above.

Figure 4:
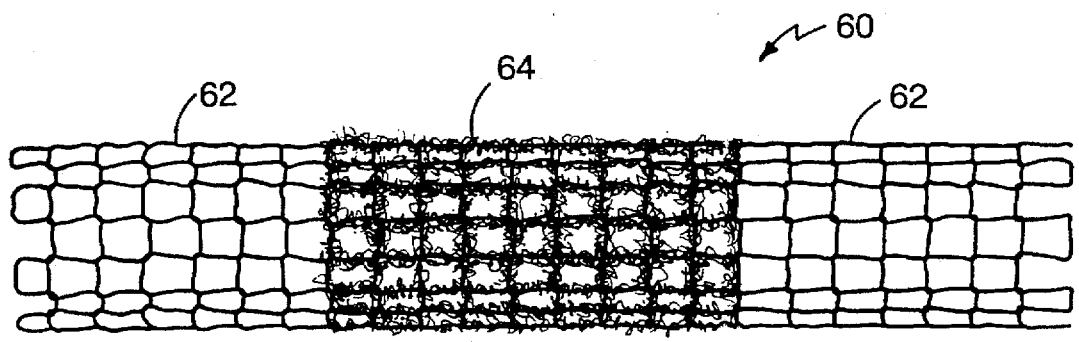
FIG. 4 is a side view of another prosthesis according to the invention.

Referring to FIG. 4, in another embodiment, rather than parallel co-knitting, stent 60 is formed by continuous knitting of a first strand 62, preferably a metal such as tantalum and a second strand 64 such as dacron in alternating regions, to perform specific functions. Metal strand 62 in the end regions provide anchoring portions while textile strand 64 provides a patent graft region.

Figure 5:
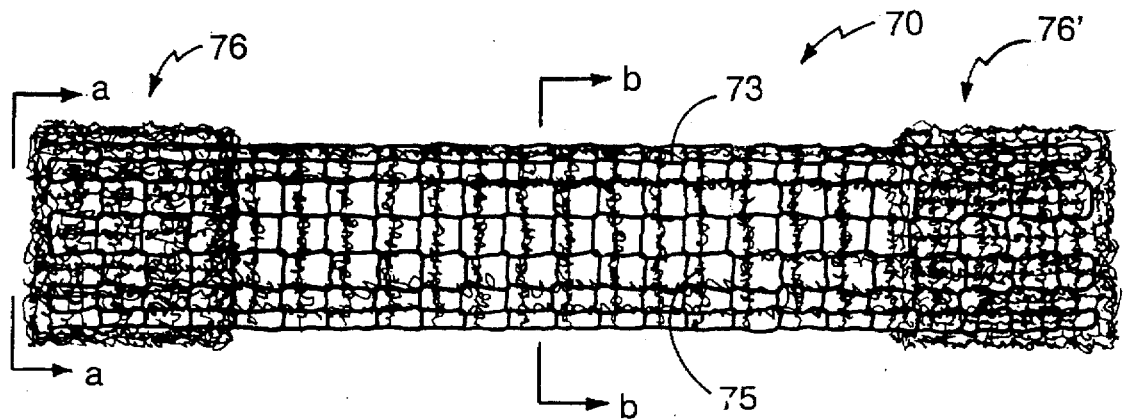
Figure 5C:
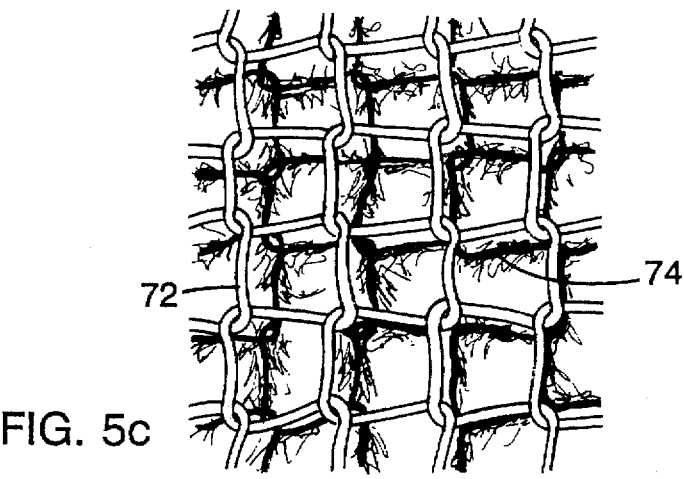
Figure 5A:
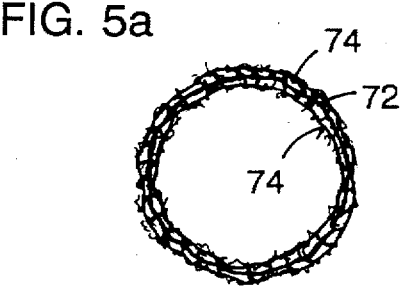
FIG. 5a is an end-on view along lines aa and FIG. 5b is a cross-sectional view along the lines bb, respectively in FIG. 5.
Figure 5B:
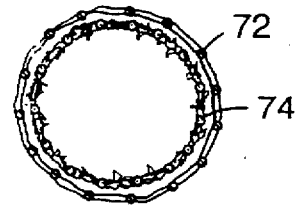

Referring to FIGS. 5–5c, in another embodiment, rather than parallel co-knitting, a graft 70 is provided that is formed of a first, separately knitted tubular structure 72 formed of a first strand 73, e.g. tantalum, and a second separately tubular knitted structure 74, assembled coaxially within the first structure 72 and formed of a second strand 75, e.g. dacron. At the ends 76, 76', the second tubular knit structure 74 is rolled over the outside of the first knit structure to form a cuff, to secure the assembly together. The first and second tubular knit structures may also be secured by sewing them together. In an alternative construction, the second tubular knitted structure of dacron could be a continuously co-knitted extension of the first metal tubular structure and the dacron knitted structure is pulled through the center of the metal structure. In other embodiments, the fabric knitted structure is on the outside of the metal knitted structure or is sandwiched between two metal structures or the metal knitted structure is between two fabric knitted structures. In another embodiment two tubular members can be effectively formed as a double knit structure.

In the embodiments of the invention discussed in the above description, the prostheses are formed of knitted strands, in other embodiments, other methods of forming a tubular structure from strands such as co-weaving, co-crocheting and the like can also be used. In some cases, with knitted embodiments or otherwise, it may be desireable to use a velour which is a variant of knitted material in which loops of yarn extend outward from the surface of the fabric formed by the knit structure.

Manufacture

Figure 6:
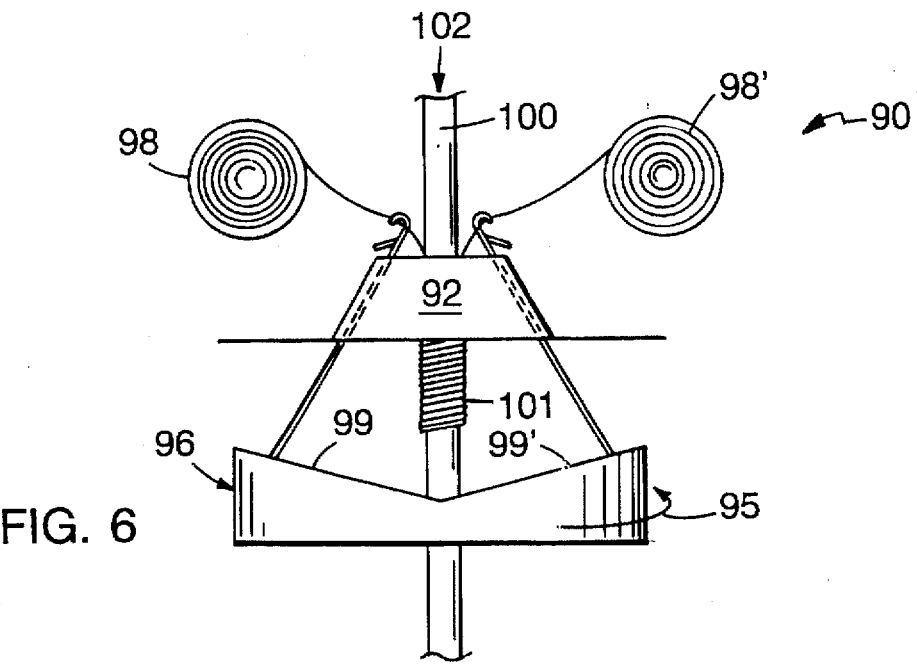

Tubular prostheses of the invention may be manufactured on a circular knitting apparatus. Referring to FIGS. 6–6e, knitting apparatus are diagrammatically shown. Referring to FIG. 6, the apparatus includes a knitting head 92 for guiding a series of needles 94, 94' which are axially extended and retracted by a rotating (arrow 95) contoured platen 96. Spools 98, 98' feed strand material to the needles during the knitting operation. The knit structure 101 is produced around a plastic mandrel 100 which is drawn downward in the direction of arrow 102.

Figures 6A, 6B, 6C, 6D:
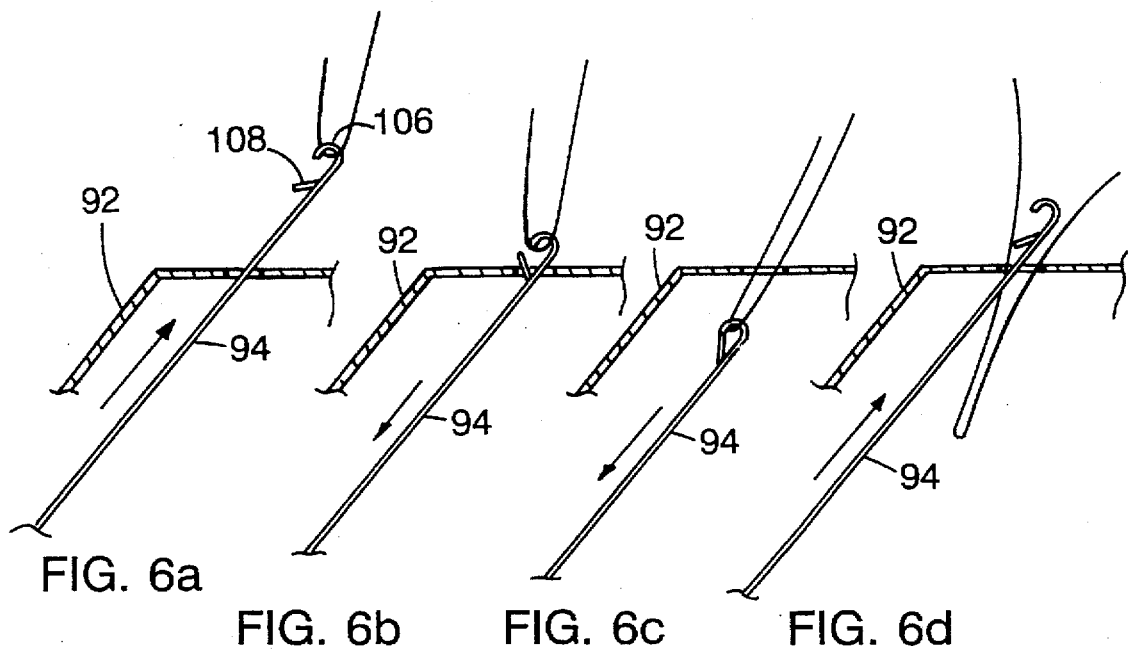
FIGS. 6a–6d illustrate.the operation of a needle used in a circular knitting machine
Figure 6E:
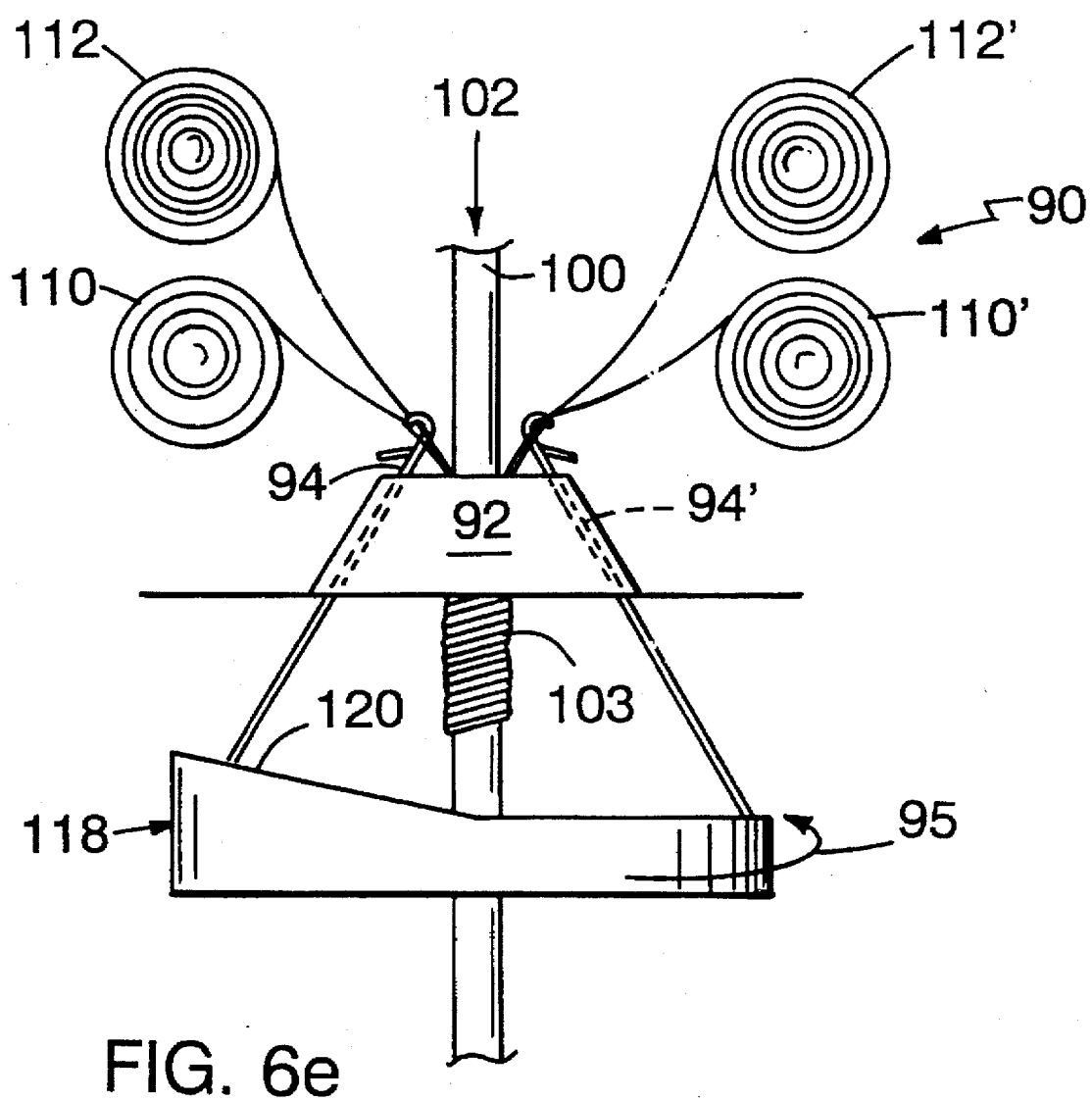
FIG. 6e illustrates a circular knitting machine configured for parallel co-knitting.

Referring particularly to FIGS. 6a–6d, the needles, such as needle 94, include a needle head 106 and a pivoted needle tongue 108. During the upstroke of the needle, the head 106 grasps a feed from the strand spool 98, the tongue 108 being initially in the downward position (FIG. 6a). On the downstroke, the tongue 108 is deflected upward as it engages the portion of the knitting head 94, thus enclosing the strand within the head (FIG. 6b). The downstroke continues for a selected length within the knitting head (FIG. 6c). On the upstroke, the strand deflects the tongue 108 downward, thus releasing the strand from the needle head 106 (FIG. 6d). The cycle is repeated as the platen 96 rotates.

The contour of the platen is selected to drive the needles for forming a desired knit pattern. In the embodiment in FIG. 6, needles 94, 94' disposed about the needle head 92 at 180° are synchronized to simultaneously pass through the stroke cycle by platen 96 which is contoured symmetrically with opposed raised sections 99, 99' and intervening valleys. By providing different strands on spools 98, 98', the knit pattern will be a continuous alternating tubular knit structure 101 such as that described with respect to FIG. 3, above.

For forming parallel co-knit structures, multiple strands are passed through each needle head to cause simultaneous parallel co-knitting. Referring to FIG. 6e, the circular knitting machine is shown configured for parallel co-knitting by providing strands from spools 110, 110', 112, 112' so that needles 94, 94' are provided simultaneously with multiple strands of different materials. A platen 118 is provided which has a single raised section 120 to sequentially drive each needle about the periphery of the knitting head through the stroke cycle. The parallel co-knit structure 103 is formed on mandrel 100. Co-knitting may be ceased by providing only a single strand to the needle heads, for example when knitting a graft such as in FIG. 1, with a co-knit wall portion and integral single knit anchoring end portions.

Generally, the number of needles circumferentially disposed around the knitting head determines the number of circumferential knit loops. The size of the needle affects the narrowness of the loops; a smaller needle forms a narrower loop since the strand bends more acutely around the narrower needle head. The diameter of the knitting head affects the diameter of the knitted stent.

Delivery

The prostheses of the invention can be positioned by various means. For example, for a balloon expandable graft with balloon expandable anchoring end portions, the graft may be positioned using a catheter with a balloon having a length substantially the length of the graft and an inflated diameter sufficient to expand the graft to the desired maximum size and to smaller sizes by partial inflation. For a graft which has a self-expanding wall portion and self-expanding anchoring ends, the graft can be restrained to small size on a catheter with a constraint such as a sleeve which is removed to release the stent at the placement site. These self-expanding grafts may be wrapped around a distal portion of the catheter in a 'jelly roll' fashion.

Figure 7:
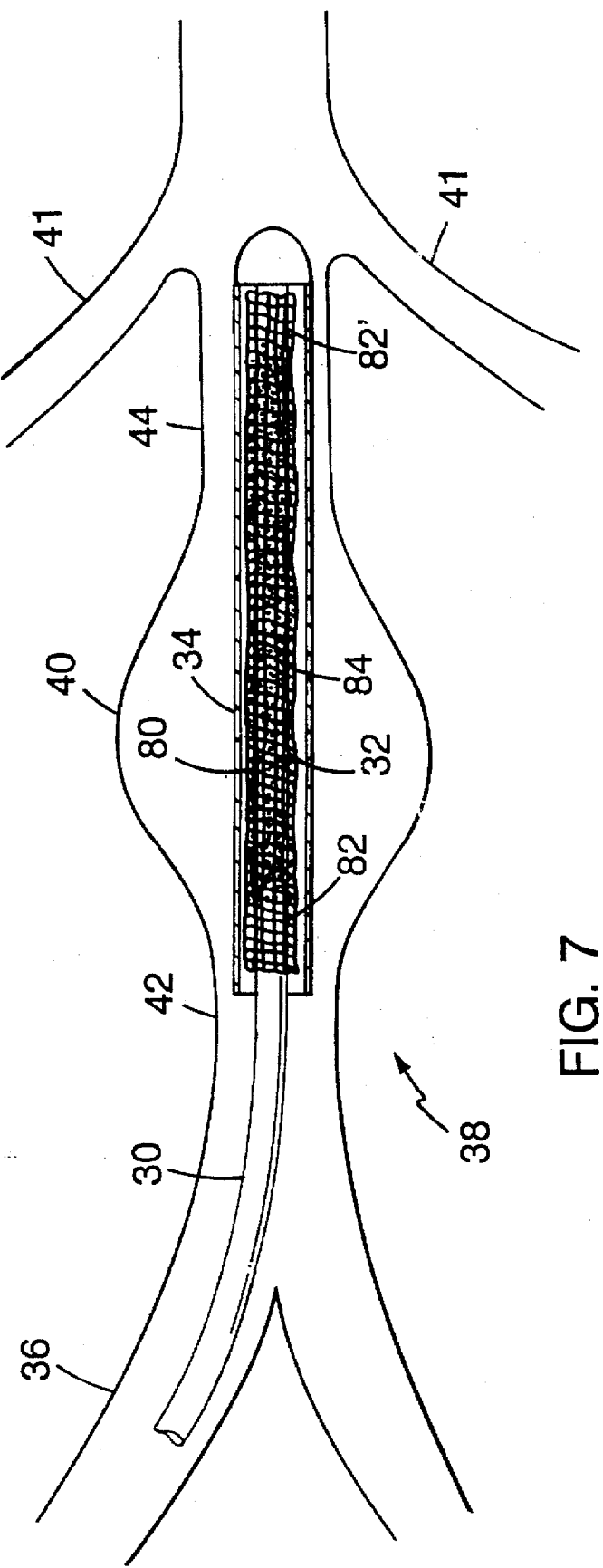
FIGS. 7–7d illustrate schematically, on a reduced scale, placement of an embodiment of an aortic graft prosthesis in the body.
Figure 7B:
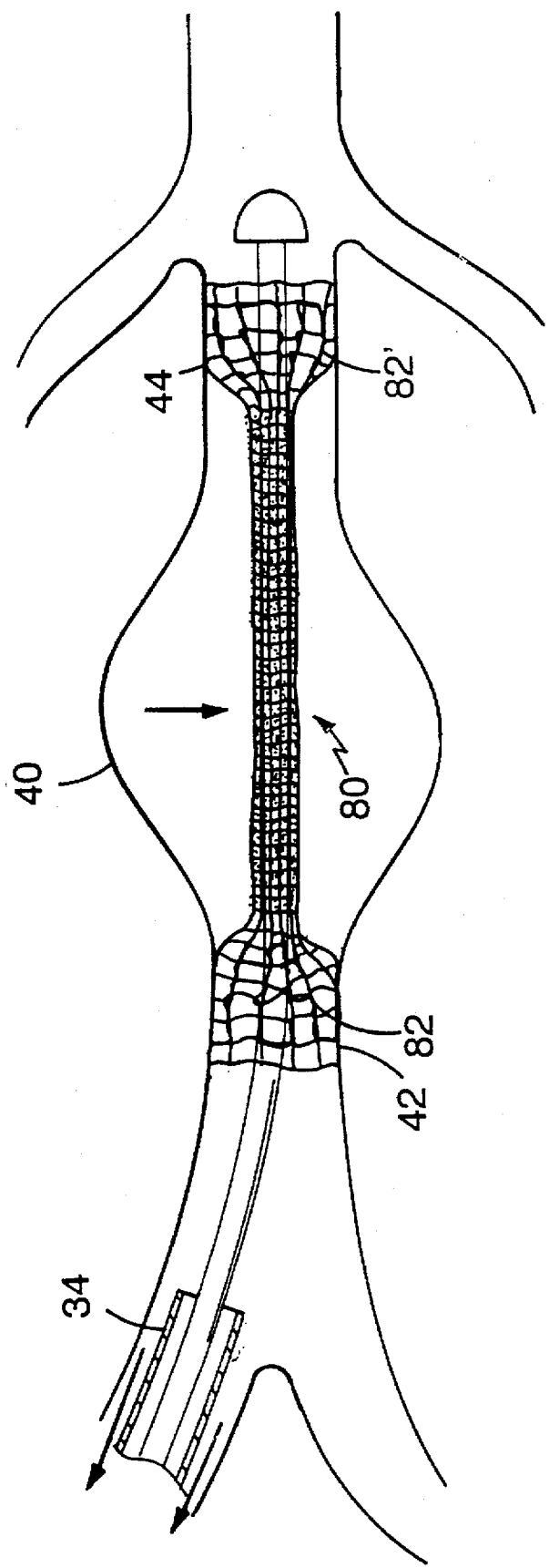
Figure 7C:
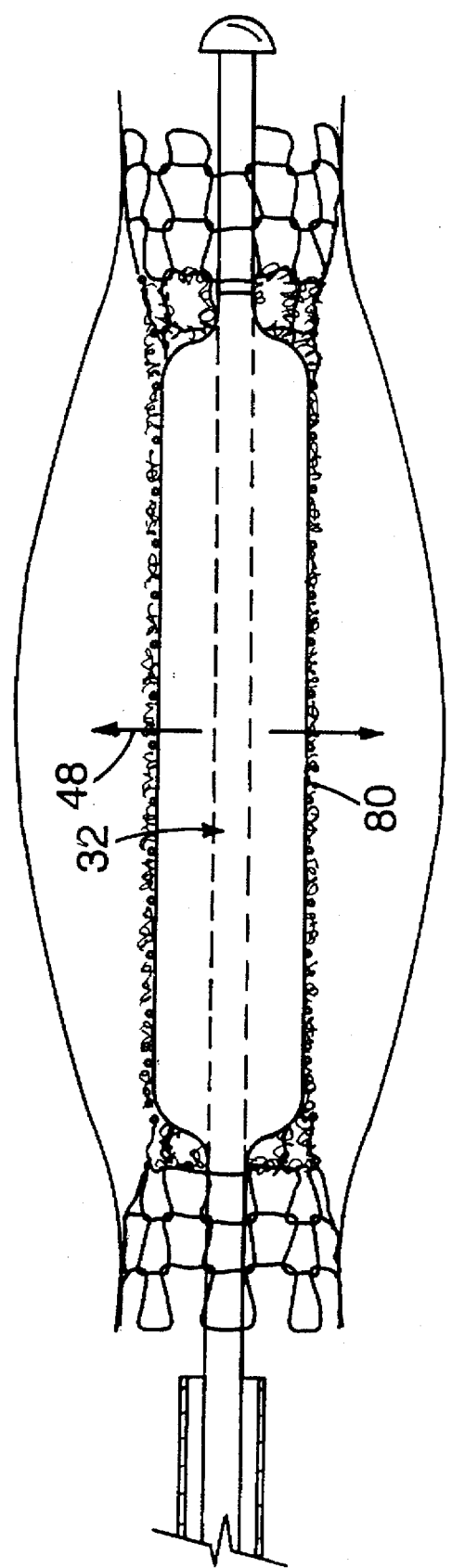
Figure 7D:
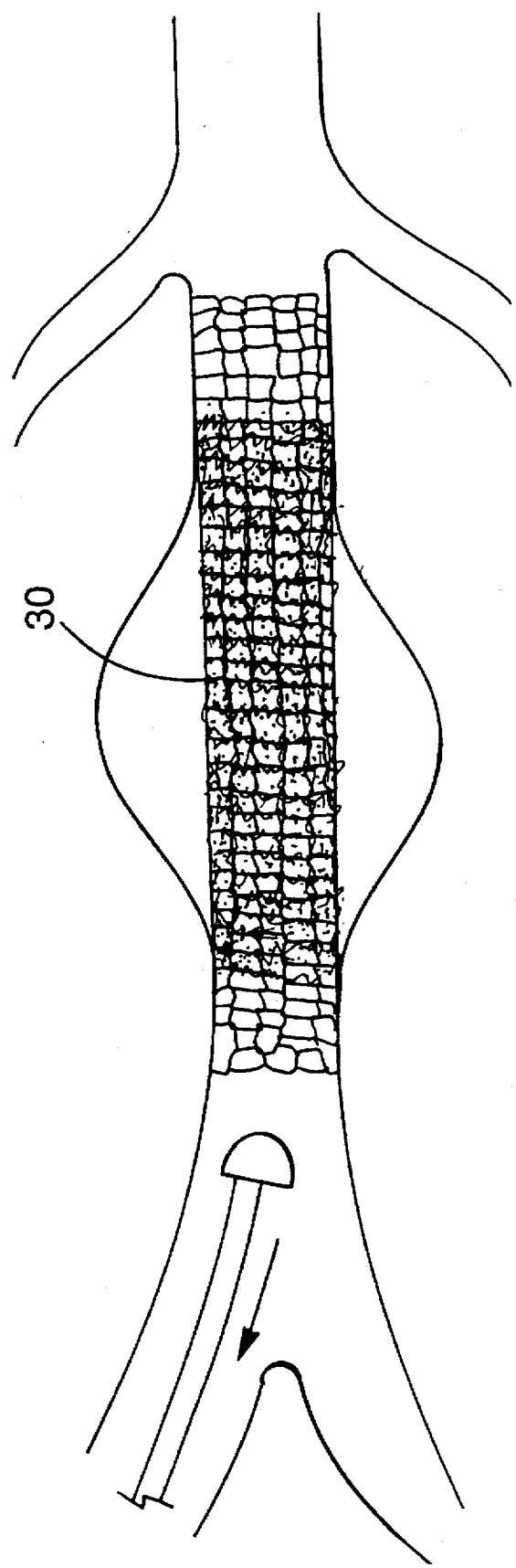

Referring to FIGS. 7–7d, positioning of a graft having self-expanding anchoring ends and a balloon expandable wall portion is illustrated. The graft 80 is positioned at the distal end of a catheter 30 which includes an inflatable balloon 32 upon which the graft is placed and an axially slidable sleeve member 34 which is placed over the graft 80 to constrain the self-expanding anchoring ends 82, 82' and a balloon wall portion formed of a co-knit tubular structure including a clot-inducing strand and a metal strand. The catheter 30, which for introduction through a vessel such as the iliac artery 36 has a diameter of about 20 French, is advanced to the aorta 38 that has been weakened by an aneurysm 40. The catheter 30 positions the graft such that graft 80 spans the region effected by aneurysm 40 and axially therebeyond to portions 42, 44 of the aorta that remain healthy but such that the graft will not interfere with the renal arteries 41. In case of an approach through the femoral artery a smaller catheter (about 12 F) is used. In this latter case, the stent is constructed with a 5 to 1 ratio of expanded to compressed size. Placement of the graft should be accurate to within about ±0.5 cm to properly position the anchoring ends 80, 80' which are typically about 1.5 cm in length on the healthy portions of the aorta.

Referring to FIG. 7a, the graft 80 is placed in the lumen by withdrawing the sleeve 34 axially (arrow 46) which releases the restraint on end portion 82' causing it to expand to engage the inner wall of the healthy portion 44 of the aorta.

Referring to FIG. 7b, with sleeve 34 completely removed from the prosthesis the anchoring end 82 similarly expands to engage the healthy portion 42 of the aorta, thus fixing the prosthesis in the lumen and positioning the wall portion 84, which remains unexpanded, at the location of the aneurysm 40.

Referring to FIG. 7c, a view in partial cross section, the balloon 32 is inflated to produce a radial force (arrow 48) which expands the wall portion 84 to a desired diameter that approximates the diameter of the healthy portions of the aorta such that the wall portion of the graft does not engage the weakened tissue of the aneurysm.

Referring to FIG. 7d, after expansion of the wall portion 84, the balloon 32 can be deflated and the catheter removed from the lumen, leaving the prosthesis 80 positioned across the aneurysm and securely anchored. As discussed above, clotting is induced by a non-metallic textured strand of the graft to fill the interstices between adjacent knitted loops within a reasonable time to form a patent covering over the wall portion of the graft.

Still other embodiments are within the following claims.

What is claimed is:

1. A prosthesis, comprising:
   a tubular member constructed to function within a body lumen, said tubular member being defined by multiple strands wherein a first strand is made of a selected metal material and a second strand is made of a different material, said first strand being arranged in a regular pattern, and said second strand being arranged in a regular pattern, and said first and second strands being loosely interlocked to form a continuous tubular wall to provide different properties at different portions along said tubular member, wherein the second strand is positioned on one surface of the tubular member at an end of the tubular member and on an opposite surface of the tubular member at a central region of the tubular member.

2. The prosthesis of claim 1 wherein said first strand material and second strand material are continuously, single knitted to form regions of said tubular knit structure formed of said first material and regions of said knit structure formed of said second material.

3. The prosthesis of claim 2 wherein said first and second strand materials are alternately knitted to form successive alternating loop rows of said first and second material.

4. The prosthesis of claim 3 wherein said second strand is formed of a body fluid-dissolvable suture material.

5. The prosthesis of claim 4 wherein said second strand is an absorbing member that includes a drug.

6. The prosthesis of claim 1 or 3 wherein said second strand material is a metal.

7. The prosthesis of claim 6 wherein said second strand material is a dense metal that enhances the radiopacity of said prosthesis.

8. The prosthesis of claim 1 wherein said first and second strand materials are formed as separate knitted loop tubular structures and said second strand knitted loop structure extends coaxially with said first strand knitted loop structure, and extends over an end of said first strand knitted loop structure to form a cuff to secure said first knitted structure to said second knitted structure.

9. The prosthesis of claim 1 wherein said second strand is non-metal material.

10. The prosthesis of claim 9 wherein said second strand is a textured textile strand.

11. A prosthesis, comprising:
    a tubular member constructed to function within a body lumen, said tubular member being defined by multiple strands wherein a first strand is made of a selected metal material and a second strand is made of a different material, said first strand being arranged in a regular pattern, and said second strand being arranged in a regular pattern, and said first and second strands being loosely interlocked to form continuous tubular wall to provide different properties at different portions along said tubular member, wherein said first and second strands are co-knit.

12. The prosthesis of claim 11 wherein said second strand is present only in a central portion of said prosthesis.

* * * * *